(12) United States Patent
Chen et al.

(10) Patent No.: US 10,082,451 B2
(45) Date of Patent: Sep. 25, 2018

(54) MICROSCOPE SLIDES WITH QUALITY CONTROLS THEREON

(71) Applicant: GE Healthcare Bio-Sciences Corp., Marlborough, MA (US)

(72) Inventors: Rui Chen, Clifton Park, NY (US); Zhengyu Pang, Clifton Park, NY (US); Colin Craig McCulloch, Niskayuna, NY (US); Michael Lazare, Niskayuna, NY (US); Robert John Filkins, Niskayuna, NY (US); Fiona Ginty, Saratoga Springs, NY (US)

(73) Assignee: GE HEALTHCARE BIO-SCIENCES CORP., Marlborough, MA (US)

( * ) Notice: Subject to any disclaimer, the term of this patent is extended or adjusted under 35 U.S.C. 154(b) by 3 days.

(21) Appl. No.: 14/778,453

(22) PCT Filed: Mar. 20, 2014

(86) PCT No.: PCT/US2014/031275
§ 371 (c)(1),
(2) Date: Sep. 18, 2015

(87) PCT Pub. No.: WO2014/165327
PCT Pub. Date: Oct. 9, 2014

(65) Prior Publication Data
US 2016/0274008 A1 Sep. 22, 2016

Related U.S. Application Data

(60) Provisional application No. 61/806,841, filed on Mar. 30, 2013.

(51) Int. Cl.
*A61B 10/00* (2006.01)
*G01N 1/31* (2006.01)
(Continued)

(52) U.S. Cl.
CPC ....... *G01N 1/312* (2013.01); *G01N 33/54393* (2013.01); *G01N 35/00663* (2013.01); *G02B 21/34* (2013.01); *G01N 2035/00673* (2013.01)

(58) Field of Classification Search
CPC ............. G01N 1/312; G01N 33/54393; G01N 35/00663; G01N 2035/00673; G02B 21/34
See application file for complete search history.

(56) References Cited

U.S. PATENT DOCUMENTS

| 5,078,969 A | 1/1992 | Bacus |
| 5,958,341 A | 9/1999 | Chu |

(Continued)

FOREIGN PATENT DOCUMENTS

| WO | 2009/085576 A2 | 7/2009 |
| WO | 2013/179279 A3 | 12/2013 |

OTHER PUBLICATIONS

Supplemental European Search Report regarding EP Application No. 14779365, dated Oct. 26, 2016, 6 pages.

(Continued)

*Primary Examiner* — Dennis White
(74) *Attorney, Agent, or Firm* — Eversheds Sutherland (US) LLP

(57) ABSTRACT

The present invention provides a microscope slide for analyzing a tissue sample. The slide includes an elongate planar substrate, which comprises a first major surface having a sample-affixing area within which a tissue sample may be affixed; a first positive control sample affixed on the first major surface at a first location adjacent to the sample-affixing area; and a second positive control sample affixed on the first major surface at a second location adjacent to the sample-affixing area. The first and second locations are spaced such that quality of the staining of the first and second positive control samples is indicative of the quality (Continued)

of the staining of the tissue sample. Also provided are a kit containing the microscope slide and a method of making and a method of using the microscope slide.

28 Claims, 16 Drawing Sheets

(51) Int. Cl.
G01N 35/00 (2006.01)
G02B 21/34 (2006.01)
G01N 33/543 (2006.01)

(56) References Cited

U.S. PATENT DOCUMENTS

| | | |
|---|---|---|
| 2005/0142654 A1 | 6/2005 | Matsumoto et al. |
| 2005/0238534 A1* | 10/2005 | Chu ............. G01N 1/312 435/6.11 |
| 2006/0127956 A1 | 6/2006 | Sompuram et al. |
| 2006/0246536 A1 | 11/2006 | Hardy et al. |
| 2007/0037138 A1* | 2/2007 | Winther ............. G01N 33/96 435/5 |
| 2010/0073766 A1* | 3/2010 | Angros ............. B01L 3/545 359/397 |
| 2011/0177548 A1 | 7/2011 | Graham et al. |
| 2013/0044200 A1 | 2/2013 | Brill et al. |
| 2013/0338014 A1 | 12/2013 | McDonough et al. |

OTHER PUBLICATIONS

International Search Report and Written Opinion regarding International Application PCT/US2014/031275, dated Aug. 15, 2014, 9 pages.
Japanese Office Action for JP Application Application No. 2016-505501 dated Jan. 24, 2018 (3 pages).

* cited by examiner

MICROSCOPE SLIDES WITH QUALITY CONTROLS THEREON

This application is a filing under 35 U.S.C. 371 of international application number PCT/US2014/031275, filed Mar. 20, 2014, which claims priority to U.S. application No. 61/806,841, filed Mar. 30, 2013, the entire disclosures of each of which are hereby incorporated by reference.

FIELD OF THE INVENTION

The present invention relates to the field of molecular pathology. More specifically, the present invention is directed to devices and methods for ensuring quality staining of a tissue sample on a microscope slide.

BACKGROUND OF THE INVENTION

Tissue diagnostics is becoming more important to patient care and requires ever more automation to meet the growing demand for throughput. Automated immunostaining technology is widely used in most IHC laboratories. The instruments are designed to mimic manual immunostaining process, including the critical steps such as antigen retrieval, antibody and solution application, incubation and washing. Different systems have varying degree of flexibility and slides capacity, but their goals are the same: minimize errors and provide high quality staining so consistent interpretation can be drawn from patient samples.

However, despite the provision of engineering control tools in these autostainers, it is not rare to have issues with incorrect dispensing of staining solution and incomplete coverage of patient samples due to air bubble or presence of thick, loose or folded tissue sections, which then creates issues of false negative and non-uniform staining for analysis. See, e.g., Shi, S.-R., Taylor, C. R., Antigen Retrieval Immunohistochemistry Based Research and Diagnostics, 2010, Wiley, Singapore. Furthermore, typical autostainers on the market limit the staining area to about 50 m m long. One manufacturer's coverslip technique limits the staining area to 21×50 mm, Another manufacturer's liquid vortex air mixing protocol covers a 25×50 mm staining area. There is currently no control method to validate that the whole tissue section within these specified staining area are stained equally or completely.

Currently the inadequate staining of tissue on a slide is only identified retrospectively. Many not-so-obvious incidents may have gone unnoticed. HercepTest™ from Dako includes a separate slide containing three pelleted, formalin-fixed, paraffin-embedded human breast cancer cell lines with staining intensity scores of 0, 1+ and 3+, which was included in each staining run as a batch control. However, batch controls cannot identify any staining defects on each individual slide within the batch.

Another previous approach prepares patient sample sections on top of slides which already contain positive or negative tissue or cell controls. Sources of these tissues vary depending on the facility and their staining behavior will differ from batch to batch due to patient variability. As shown in FIG. 1, the prior art provides a tissue sample slide 1 having a planar substrate 2 on which are affixed a tissue sample 3 and a cell control 4. The cell control 4 is in the form of cell pellets affixed to the slide in a region between the sample and one longitudinal end 5 of substrate 2. FIG. 2 depicts another tissue sample slide 1' of the prior art, sold by Bio-Quick Corporation of Rockville, Md., which includes a 9-dot array of cell controls 4a-i for cancer marker IHC assays (http://www.bio-quick.com/qc-dots%C2%AE-cancer-array-ca-control-slides). Cell controls 4a-i can include positive and negative controls but are each shown to be distinct controls from each other. Although slide 1' contains cell pellets arrays, it offers similar information as a slide containing a single cell pellet. That is, the cell pellet markers are solely used for calibration of the signals received from the tissue sample being analyzed. Like for slide 1, slide 1' positions controls 4a-I between the sample and one longitudinal end 5' of the substrate 2' and may thus be near or far away from the patients' sample depending on the size of sample and skills of the operator. The location of these controls to a single side of the tissue thus does not provide a reliable indication of whether or not the tissue sample itself was stained completely and uniformly.

The art therefore lacks a slide which uses the controls in a manner to assure a tissue sample has been stained in its entirety, both completely and uniformly.

SUMMARY OF THE INVENTION

The present invention provides a microscope slide with positive control samples adjacent to a sample-affixing area. These slides are suitable for analysis of tissue samples, such as pathology staining, and provide real-time confirmation on staining quality. The positive control samples or positive controls include one or more biomarkers that may be detected during the analysis of the tissue sample. Thus, lack of staining from the positive controls will provide real-time identification of staining failures. Optionally, negative control samples may also be included on the slide. The negative control samples or negative controls do not contain the one or more biomarkers found in the positive controls. Staining from the negative controls therefore also provide real-time identification of staining failures.

Thus, in one aspect, the invention provides a microscope slide for a tissue sample to be stained. The microscope slide includes an elongate substantially planar substrate, which substrate includes a first major surface having a sample-affixing area within which a tissue sample may be affixed. The slide further includes a first positive control sample affixed on the first major surface at a first location adjacent to the sample-affixing area and a second positive control sample affixed on the first major surface at a second location adjacent to the sample-affixing area. The first and second locations are spaced such that quality of the staining of the first and second positive control samples is indicative of the quality of the staining of the tissue sample.

In another aspect, the invention provides a microscope slide for a tissue sample to be stained. The microscope slide includes an elongate substantially planar substrate, which substrate includes a first major surface having a sample-affixing area within which a tissue sample may be affixed. The slide includes a first positive control sample affixed on the first major surface at a first location adjacent to the sample-affixing area and a second positive control sample affixed on the first major surface at a second location adjacent to the sample-affixing area. The first and second locations are spaced such that at least a portion of the sample-affixing area extends between the first and second locations along the longitudinal axis of the substrate.

In yet another aspect, the invention provides a method of fabricating a microscope slide of the present invention, which method includes the steps of transferring and affixing a thin layer of a positive control sample onto the microscope slide at a first location and a second location wherein the first and second locations are spaced such that quality of the staining of the first and second positive control samples is indicative of the quality of the staining of the tissue sample.

In still another aspect, the invention provides a method of analysis, which method includes the steps of staining a microscope slide of the present invention with a detection means for positive control samples positioned at first and second locations, respectively. The first and second locations are spaced such that quality of the staining of the positive control samples is indicative of the quality of the staining of the tissue sample, and detecting the positive control samples from the at least first and second location.

DETAILED DESCRIPTION OF THE PREFERRED EMBODIMENTS

The present invention provides a microscope slide comprising an innovative control sample layout which provides higher confidence of proper staining of a tissue sample affixed to the slide. A slide of the present invention is suitable for automated staining and analyses of the tissue sample. The microscope slides of the present invention are especially suited for automated, multi-round, multiplexed analysis of a tissue sample. These slides enable confirmation on staining quality during tissue imaging/analysis. These slides also provide for confirmation of staining quality after all rounds of staining are complete by review of the images provided after each round of staining. In some embodiments, the microscope slide and the methods disclosed herein may be particularly applicable in histochemistry, immunostaining, immunohistochemistry, immunoassays, immunofluorescence or fluorescence in situ hybridization.

Figure 1:
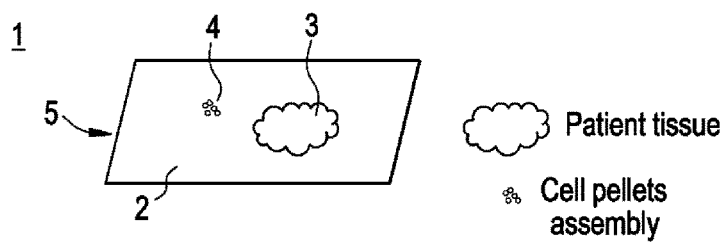
FIG. 1 depicts a slide of the prior art having a cell pellet as a control at a location adjacent to the tissue-affixing area of the slide.
Figure 2:
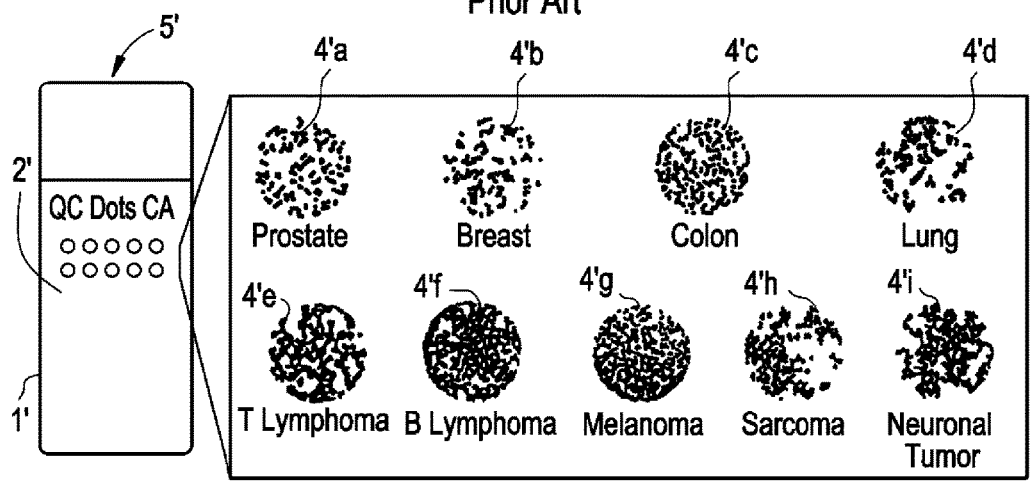
FIG. 2 depicts another slide of the prior art having multiple cell pellets at a location adjacent to the tissue-affixing area of the slide.
Figure 3:
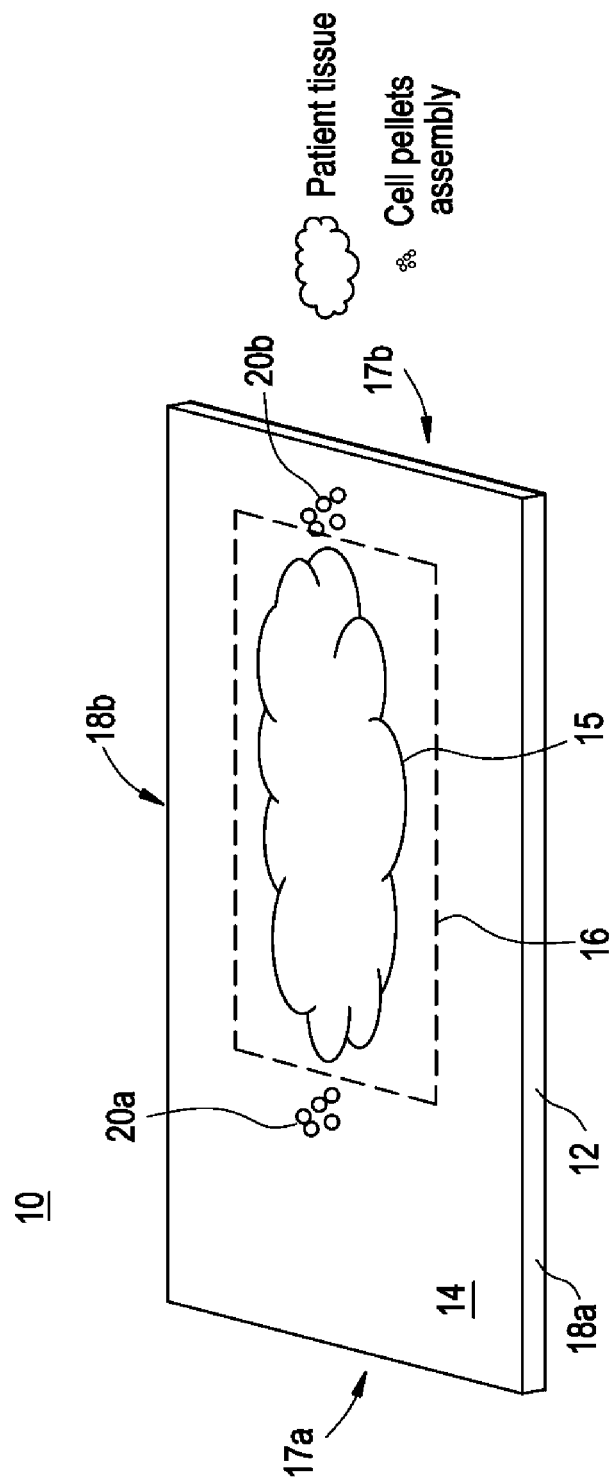
FIG. 3 depicts a slide according to an embodiment of the present invention having cell pellets positioned across a portion of the tissue-affixing area of the slide.

As shown in FIG. 3, a first aspect of the present invention provides a microscope slide 10 for staining a tissue sample 15 affixed thereof. Slide 10 includes an elongate substantially planar substrate 12 having a first major surface 14 having a sample-affixing area 16 (the perimeter of which is indicated by phantom line) within which tissue sample 15 may be affixed, Slide 10 further provides a first positive control sample 20a affixed on first major surface 14 at a first location adjacent to sample-affixing area 16, and a second positive control sample 20b affixed on first major surface 14 at a second location adjacent to sample-affixing area 16. The first and second locations are spaced such that quality of the staining of first and second positive control samples 20a and 20b is indicative of the quality of the staining of tissue sample 15. That is, as control samples 20a and 20b are positioned between tissue sample 15 and the longitudinal edges 17a and 17b, respectively, of substrate 12, the detection of signals in both control samples 20a and 20b after staining of tissue sample 15 indicates that the stain coverage included both ends of substrate 12, a better indicia of complete staining of tissue sample 15 than if only a single control sample located at a single adjacency demonstrates staining. By providing multiple positive control samples about the tissue-affixing area of a substrate, the present invention provides greater confidence of complete tissue staining when the controls about the tissue sample each demonstrate having been stained. The lack of a detected signal from a positive control sample would be indicative of a failure to completely stain the tissue sample. Staining of the control samples will be evident during imaging of the tissue on the substrate after each round of staining, thus providing real-time confidence that the tissue itself was properly stained. Additionally, as the images will be retained for subsequent analysis, the present invention will allow the provision of a record of the control sample staining should further review be warranted.

Desirably, the first and second locations are spaced such that at least a portion of sample-affixing area 16 extends between the first and second locations along the longitudinal axis of substrate 12. The term 'longitudinal axis of substrate 12' means a line extending centrally along the elongate length of substrate 12 between opposed ends 17a and 17b. For purposes of this description, the longitudinal axis of substrate 12 is further contemplated to extend along major surface 14. Therefore, there will be a longitudinal spacing of the locations such that at least a portion of sample-affixing area 16 extends longitudinally between them. As will be described herein, such longitudinal spacing of the first and second locations may further include a transverse spacing between the locations, i.e., where at least one of the locations is spaced between the longitudinal axis and an elongate edge 18a or 18b of substrate 12. In each of these embodiments the first and second locations are considered to be spaced along the longitudinal axis of the slide even when either one or both are also transversely spaced from the longitudinal axis. For each embodiment of the present invention, a line extending between control samples 20a and 20b will cross through sample-affixing area 16. The present invention contemplates that confidence of proper staining of tissue sample 15 may be higher still if a portion of the tissue sample is located along the line between two control samples.

The present invention contemplates that substrate 12 of microscope slide 10 is formed from a material suitable for tissue staining and analysis, such as a glass suitable for laboratory glassware. Substrate 12 is desirably a substantially planar member and, except for certain embodiments noted below, major surface 14 is desirably a planar surface. While substrate 12 is depicted having a rectangular shape, the present invention further contemplates that substrate 12 may have a circular shape or other shape with non-linear edges or a single continuous non-linear edge.

For all embodiments of the microscope slide of the present invention, the tissue-affixing area is indicated by a phantom (dashed) line showing its indicated perimeter. No line need appear on the major surface of the slide substrate although the present invention contemplates that the actual tissue-affixing area may be designated by a line on the major surface or by a microchannel etched into the major surface. Additionally, while the shape of the tissue-affixing area is typically shown as being substantially rectanglular, the shape of the perimetrical boundary of the tissue-affixing area may be any shape (such as oval or circular) providing sufficient surface area to contain the tissue sample (or the portion thereof) to be analyzed. The present invention contemplates that the positioning of the control samples on the major surface of the substrate will indicate to a user the area within which the tissue sample should be affixed so as to be properly positioned according to the present invention. Similarly, while the patient tissue sample is illustrated by a generally oval shape, it is envisioned that the patient sample may be any shape, such as circular, square, rectangle or irregular. The shape of the patient sample does not affect aspects of the invention. The layout of the positive control samples may be adjusted accordingly based on the dimension and format of the patient sample to achieve the effect desired, i.e., controlling staining variability of patient samples.

Moreover, the present invention contemplates that the positive control samples employed by the present invention are desirably selected from cell pellet, control tissue sample, or carrier loaded with biomaterials such as cell homogenates, peptides, proteins and DNAs. The carriers can be particles, gels or other format. Patient's tissue sample can be sectioned onto these slides, of which the positive control samples will provide real-time identification of staining failures such as inconsistent staining solution dispensing and concerns regarding boundary staining for large tissue samples.

The first and second positive control samples preferably contain at least one biomarker (i.e., marker) in common. By biomarker or marker, it is meant to include any cellular component which may be detected by a detection means. Exemplary cellular components include proteins, nucleic acid molecules, or carbohydrates. Preferably, this common biomarker may be detected by the same detection means for detecting the tissue sample. Alternatively, the first and the second positive control sample may contain different biomarkers. The present invention contemplates that as long as both positive control samples are both detectable by some detection means, the goal of the present invention, i.e., identification of staining failures, is fulfilled. Thus, the present invention contemplates that it is not necessary that the first and second positive control samples be the same, or include cell pellets formed of the same cell lines, so long as they contain a common biomarker. Alternatively, even if the first and second positive control samples contain completely different biomarkers, staining failure may be identified using the present method as long as the controls may both be detected when the tissue sample is analyzed.

The present invention further contemplates that each positive control sample may itself contain two or more different kinds of biomarkers e.g., antigen. While each cell line may be detected by a variety of detection means, the present invention further contemplates that cell lines expressing different kinds of antigens may be mixed together to generate cell pellets. These positive control samples are especially useful for multiplexed experiments. Thus, a first marker is detected in both positive control samples as the positive control for the first round of the multiplexed experiment. A second marker is detected in both positive control samples as the positive control for the second round of the multiplexed experiment and so on.

It will thus be understood that each marker provided in a control sample of the present invention will include a corresponding paired associate marker positioned across a portion of the tissue-affixing area of the slide substrate. As discussed above, the paired associate markers may be the same. Alternatively, the paired associate markers may be different biomarkers, as long as they are capable of been both detected when the tissue sample is analyzed.

Figure 4:
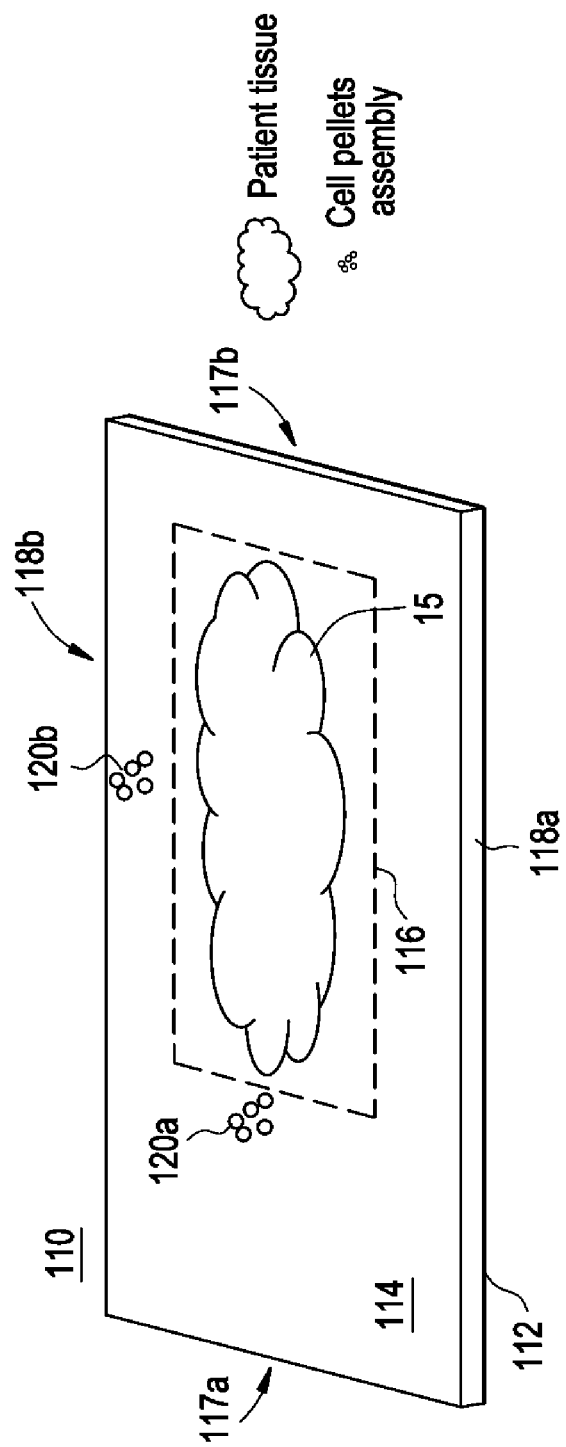
FIG. 4 depicts another slide according to an embodiment of the present invention having cell pellets positioned across a portion of the tissue-affixing area.

As shown in FIG. 4, the present invention further provides a microscope slide 110, where like numbering denotes like components to other embodiments of the present invention. For all embodiments of the present invention, the applied tissue sample will always be numbered as '15'. The term 'like numbering' indicates that like components of the different embodiments of the slides sharing the last two-digits of their designation will typically be similar to each other. Similarly, components with the same last two-digits in their designation may further be designated by a suffix letter which indicates that these components are substantially the same in construction or make-up but distinctly provided.

Slide 110 includes a substantially planar substrate 112 having a planar major surface 114. Major surface 114 includes a sample-affixing area 116 where a tissue sample 15 may be affixed by conventional means. Slide 110 includes first and second positive control samples 120a and 120b provided at first and second locations of major surface 114, respectively. First positive control samples 120a is between sample-affixing area 116 and first longitudinal edge 117a of substrate 112 and second positive control sample 120b is located transversely alongside sample-affixing area 16. By 'located transversely-alongside', it is meant that the location is positioned between the sample-affixing area 116 and one of transverse edges 118a and 118b of substrate 112, along a line transverse to the elongate axis of substrate 112.

Figure 5:
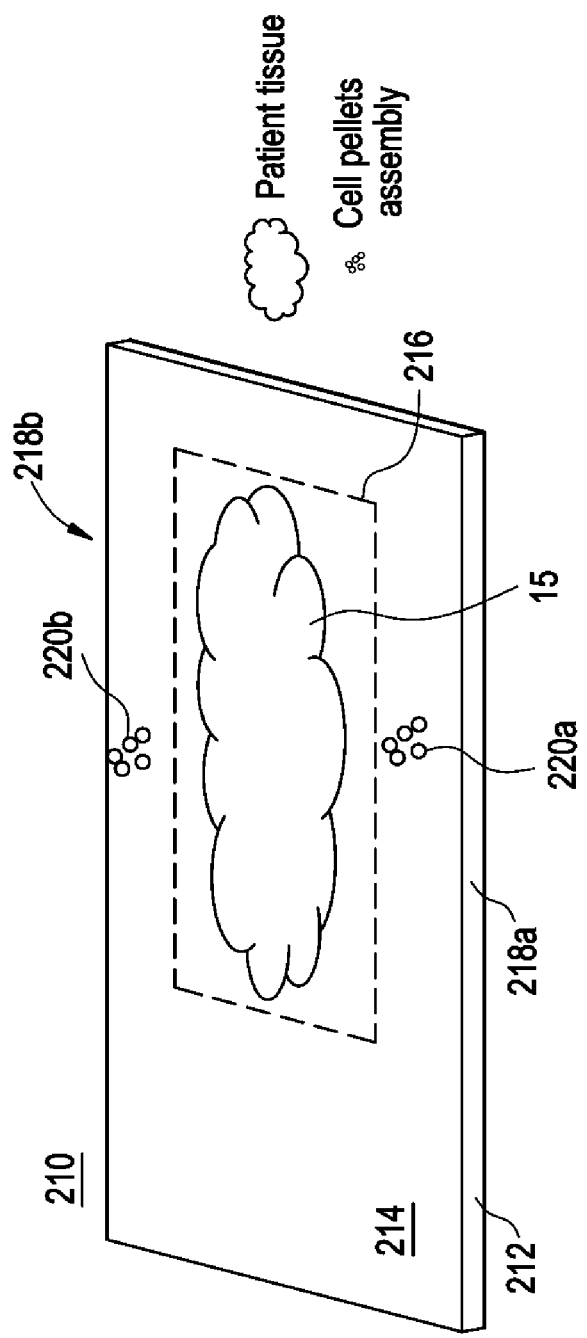
FIG. 5 depicts yet another slide according to an embodiment of the present invention having cell pellets positioned opposite the tissue-affixing area from each other and along opposed edges of the slide.

As shown in FIG. 5, the present invention further contemplates a microscope slide 210 designed such that the first and second locations for affixing the first and second positive control samples 220a and 220b are on opposing sides of sample-affixing area 216 on major surface 214, i.e, the locations are substantially transversely-spaced across sample-affixing area 216. Once again, like numbering denotes like components of the present invention. As shown in FIG. 5, control sample 220a is positioned between sample 15 and edge 218a of substrate 212 while control sample 220b is oppositely positioned between sample 15 and edge 218b of substrate 212.

Figure 6:
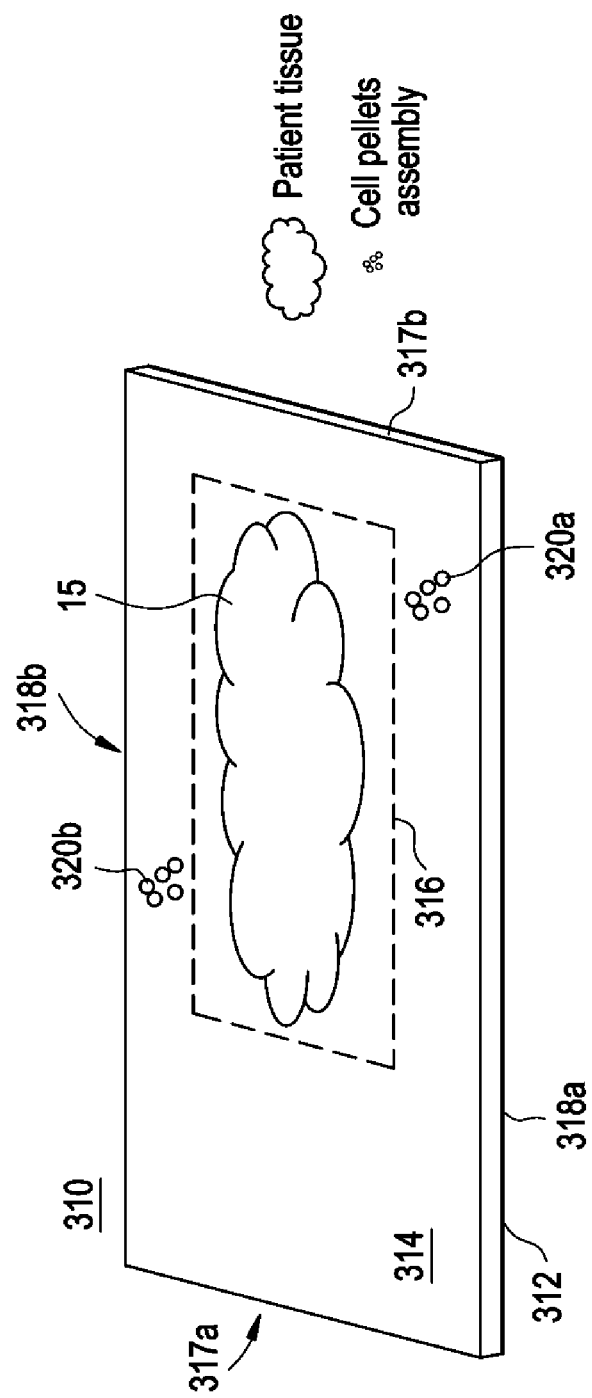
FIG. 6 depicts an alternate embodiment of the slide of FIG. 5, with the cell pellets being both longitudinally spaced from each other and transversely spaced from the longitudinal axis of the slide.

FIG. 6 depicts another microscope slide 310 of the present invention. Slide 310 includes a substantially planar substrate 312 including a first major surface 314 having a tissue sample-affixing area 316 for receiving a tissue sample to be analyzed. Slide 310 further includes first and second control samples 320a and 320b positioned at first and second locations on surface 314, respectively. The first and second locations are both longitudinally spaced along the longitudinal axis of the substrate as well as spaced transversely, or to either side, of the longitudinal axis. That is, control sample 320a is shown to be located closer to longitudinal end 317b and edge 318a as compared to control sample 320b which is located closer to longitudinal end 317a and edge 318b. The first and second locations are substantially diagonally across sample-affixing area 316 from each other, i.e., both longitudinally and transversely spaced across sample-affixing area 316, although the present invention contemplates that the term 'diagonally' simply indicates that a line drawn between the two locations could be said to pass through two non-adjacent edges of a polyhedron bounding a tissue sample.

Figure 7:
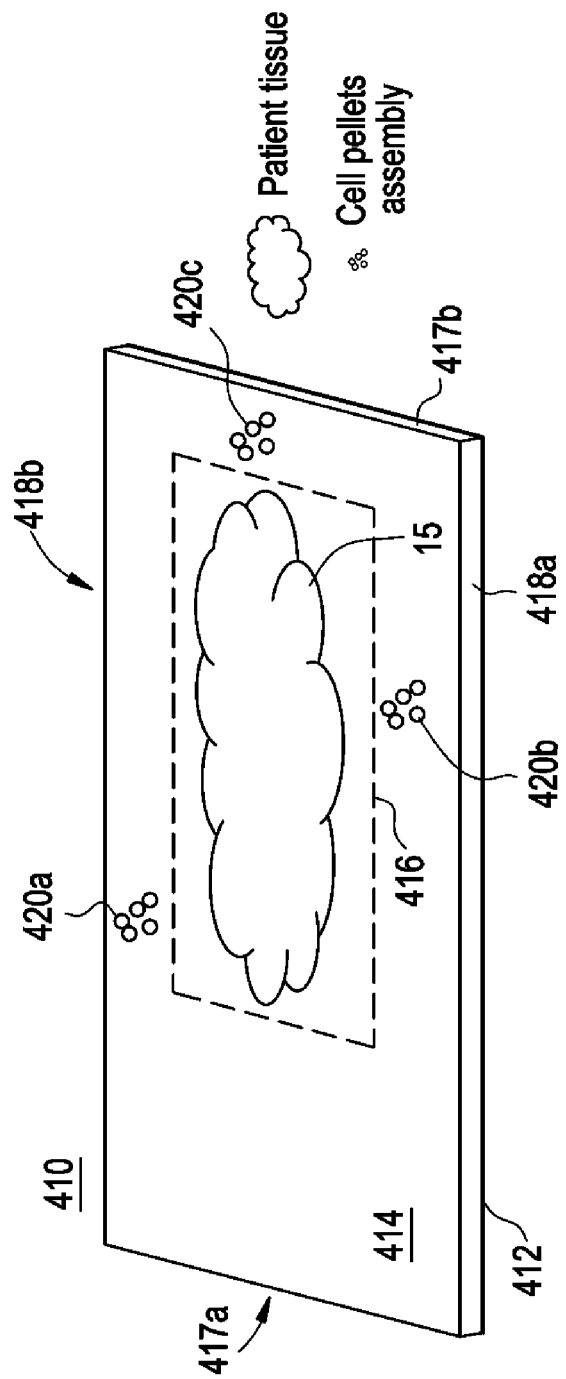
FIG. 7 depicts another embodiment of the present invention having three cell pellets positioned about the tissue-affixing area of the slide.

FIG. 7 depicts yet another microscope slide 410 of the present invention, with like numbering representing like components. Slide 410 includes a substantially planar substrate 412 including a first major surface 414 having a tissue sample-affixing area 416 for receiving a tissue sample 15 to be analyzed. Slide 410 further includes first, second, and third control samples 420a, 420b, and 420c positioned at first, second, and third locations on surface 414, respectively. The longitudinal and transverse spacing of control samples 420a, 420b, and 420c desirably ensures that line segments extending between the three locations each pass through sample-affixing area 416. The present invention further contemplates that two of the control samples may be positioned adjacent to each other such that a line segment between them does not pass through sample-affixing area 416, although it is desirable that none of the three control samples share a common ordinate on major surface 414 so as to provide further confidence of complete tissue staining when all three evidence staining.

While control samples 420a-c are indicated as comprising the same biomarkers, the present invention further contemplates for embodiments providing three or more control samples about the tissue affixing area, that each of the control samples may further provide different combinations of biomarkers without departing from the instant invention. By way of illustration and not of limitation, a first control sample may include biomarkers "X" and "Y", a second control sample may include biomarkers "Y" and "Z" while a third control sample includes biomarkers "Z" and "X". By employing three such distinct control samples about the tissue affixing area according to the present invention, the paired biomarkers "X", "Y" and "Z" can provide a higher degree of confidence of a stain covering the tissue sample. Thus, while it may be desirable that each control sample employed have the same composition to one or more other control samples, the combination of biomarkers within a control sample may be varied so long as the distribution of the biomarkers of the control samples about the tissue-affixing area provides two or more biomarkers located across a portion of the tissue-affixing area according to the present invention.

Figure 8:
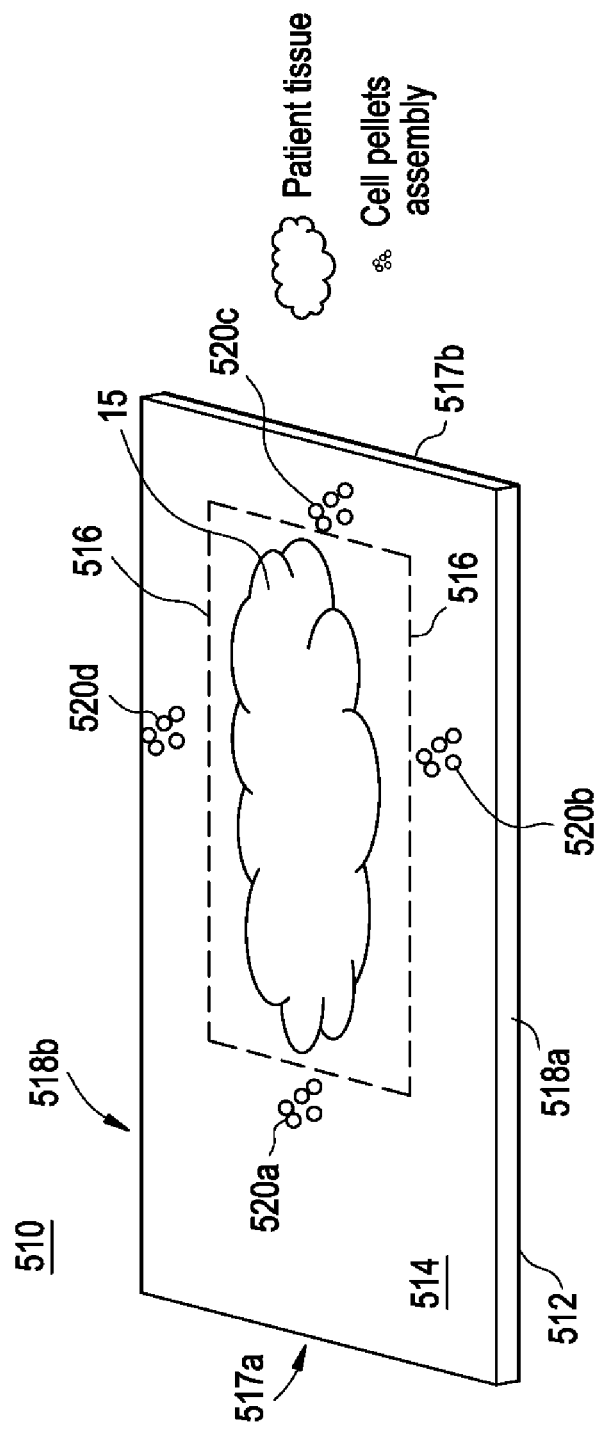
FIG. 8 depicts still another slide according to an embodiment of the present invention, having four cell pellets positioned about the tissue-affixing area of the slides.

FIG. 8 depicts yet another microscope slide 510 of the present invention. Slide 510 includes a substantially planar substrate 512 including a first major surface 514 having a tissue sample-affixing area 516 for receiving a tissue sample 15 to be analyzed. Slide 510 further includes first, second, third and fourth positive control samples 520a, 520b, 520c, and 520d positioned at first, second, third and fourth locations on surface 514, respectively. The longitudinal and transverse spacing of control samples 520a, 520b, 520c and 520d desirably ensures that line segments extending between the four locations each pass through sample-affixing area 516. The present invention further contemplates that two or three of the control samples may be positioned adjacent to each other such that a line segment between them does not pass through sample-affixing area 516, although it is desirable that none of the four control samples share a common ordinate on major surface 514 so as to provide further confidence of complete tissue staining when all four evidence staining.

As will be appreciated by those of ordinary skill in the art, the present invention also contemplates that, in certain embodiments, the two or more positive control samples may form substantially continuous line that surrounds the entire perimeter of sample-affixing area. The precise number and spacing of control samples used to perimetrically bound the sample-affixing area may thus be chosen as desired.

Figure 9:
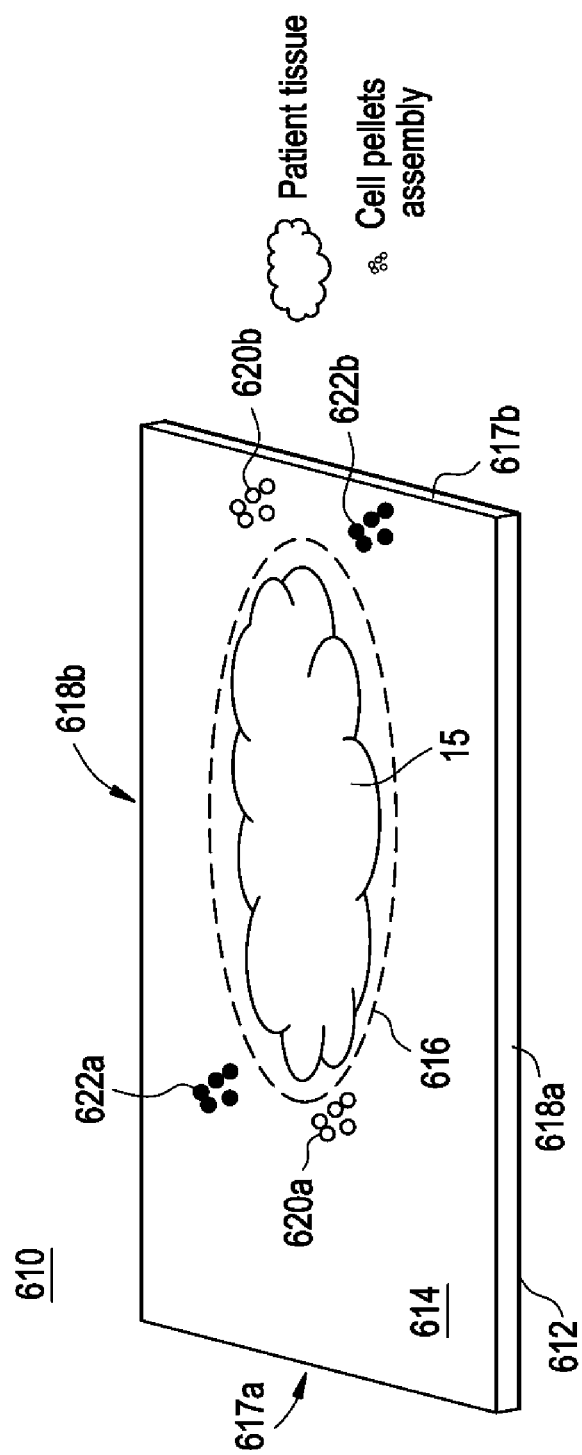
FIG. 9 depicts still yet another slide according to an embodiment of the present invention, having pairs of different cell pellets positioned across the tissue-affixing area from each other.

As shown in FIG. 9, the present invention further contemplates a microscope slide 610 designed such that in addition to the first and second locations for affixing the first and second positive control samples 620a and 620b, the microscope slide 610 further includes a third and fourth locations for affixing a third and fourth control samples 622a and 622b. Once again, like numbering denotes like components of the present invention. As shown in FIG. 9, the first and second positive control samples 620a and 620b contain a common biomarker that may be detected by the same detection means. The present invention contemplates that the third and fourth control samples 622a and 622b may contain a common biomarker different from that in the control samples 620a and 620b. Alternatively, the third and fourth control samples 622a and 622b may contain the same biomarker as that of the first and second positive control samples, albeit at a different signal level. The third and fourth control samples 622a and 622b may also serve as negative controls as that of the first and second positive control samples.

As shown in FIG. 9, the slide 610 includes a substantially planar substrate 612 including a first major surface 614 having a tissue sample-affixing area 616 for receiving a tissue sample 15 to be analyzed. The first and second locations are both longitudinally spaced along the longitudinal axis of the substrate as well as spaced transversely, i.e., spaced to either side of, or with respect to, the longitudinal axis. That is, control sample 620a is shown to be located closer to longitudinal end 617a and edge 618a as compared to control sample 620b which is located closer to longitudinal end 617b and edge 618b. The first and second locations are substantially diagonally across sample-affixing area 616 from each other, i.e., longitudinally spaced across sample-affixing area 616, although the present invention contemplates that the precise location need not be so geometrically limited as being precisely opposite each other across area 616. Similarly, the third and fourth locations are both longitudinally spaced along the longitudinal axis of the substrate as well as spaced transversely, or to either side, of the longitudinal axis. That is, control sample 622a is shown to be located closer to longitudinal end 617a and edge 618b as compared to control sample 622b which is located closer to longitudinal end 617b and edge 618a. The third and fourth locations are substantially diametrically across sample-affixing area 616 from each other, i.e., longitudinally spaced across sample-affixing area 616, although the present invention contemplates that the precise location need not be so geometrically limited as being precisely opposite each other across area 616.

Figure 10:
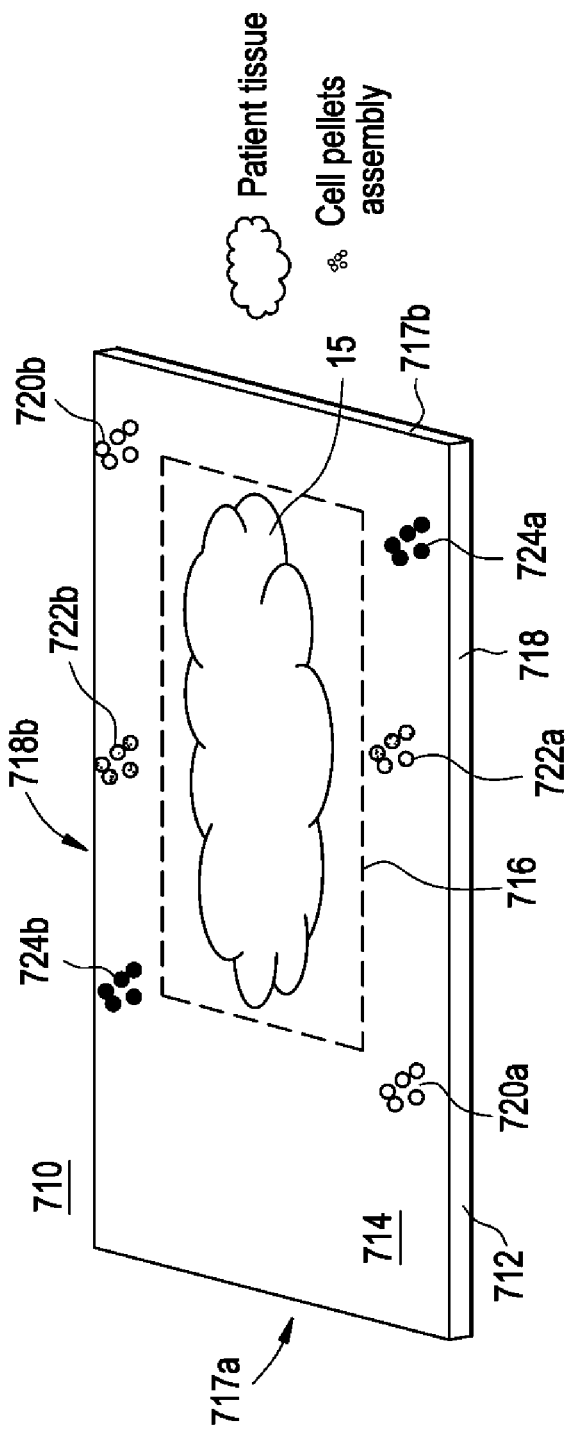
FIG. 10 depicts even yet another slide according to an embodiment of the present invention, having multiple pairs of different cell pellets positioned along opposing edges of the slide and adjacent to the tissue-affixing area.

As shown in FIG. 10, the present invention further contemplates a microscope slide 710 designed such that in addition to the first, second locations for affixing the first and second positive control samples 720a and 720b, the third and fourth locations for affixing a third and fourth control samples 722a and 722b, the microscope slide 710 further includes a fifth and sixth locations for affixing a fifth and sixth control samples 724a and 724b. Once again, like numbering denotes like components of the other embodiments of the present invention. As shown in FIG. 10, the first and second positive control samples 720a and 720b contain a common biomarker that may be detected by the same detection means. The present invention contemplates that the third and fourth control samples 722a and 722b may contain a common biomarker different from first and second control samples 720a and 720b, and that the fifth and sixth control samples 724a and 724b may contain a common biomarker that is different still. Alternatively, the third and fourth control samples 722a and 722b as well as the fifth and sixth control samples 724a and 724b may contain the same biomarker as that of the first and second positive control samples, albeit at different signal levels. One pair of the third and fourth control samples 722a and 722b, or the fifth and sixth control samples 724a and 724b may also serve as negative controls.

As shown in FIG. 10, slide 710 includes a substantially planar substrate 712 including a first major surface 714 having a tissue sample-affixing area 716 for receiving a tissue sample 15 to be analyzed. The first and second locations are both longitudinally spaced along the longitudinal axis of the substrate as well as spaced transversely, or to either side, of the longitudinal axis. That is, control sample 720a is shown to be located closer to longitudinal end 717a and edge 718a as compared to control sample 720b which is located closer to longitudinal end 717b and edge 718b. The first and second locations are substantially diametrically across sample-affixing area 716 from each other, i.e., longitudinally spaced across sample-affixing area 716, although the present invention contemplates that the precise location need not be so geometrically limited as being precisely opposite each other across area 716.

The third and fourth locations for affixing the third and fourth positive control samples 722a and 722b are on opposing sides of sample-affixing area 716 on major surface 714. I.e., the locations are substantially transversely-spaced across sample-affixing area 716. Control sample 722a is positioned between sample 15 and edge 718a of substrate 712 while control sample 722b is oppositely positioned between sample 15 and edge 718b of substrate 712.

Similar to the first and second locations, the fifth and sixth locations are both longitudinally spaced along the longitudinal axis of the substrate as well as spaced transversely, or to either side, of the longitudinal axis. That is, control sample 724a is shown to be located closer to longitudinal end 717b and edge 718a as compared to control sample 724b which is located closer to longitudinal end 717a and edge 718b. The fifth and sixth locations are substantially diametrically across sample-affixing area 716 from each other, i.e., longitudinally spaced across sample-affixing area 716, although the present invention contemplates that the precise location need not be so geometrically limited as being precisely opposite each other across area 716.

As illustrated in FIGS. 9 and 10 above and FIG. 12 below, two or more positive control samples containing different amounts of biomarker e.g. antigen levels (as opposed to the previously-discussed different types of biomarkers) may be included on the microscope slide. In such embodiments, each control sample type is provided in at least pairs such that the pairs of like control samples are located across some portion of the tissue-affixing area. For example, different cell lines with different levels of antigen expression may be chosen to generate individual cell pellets. Alternatively, the same cell line with a different amount of cells may be chosen to generate different cell pellets. These cell pellets may be arranged in a pre-determined pattern about the sample-affixing area. Thus, the controls may contain low, medium, or high levels of a certain biomarker. Alternatively, the controls may contain zero, medium or high levels of a certain biomarker. These control samples may be quantified and the results compared to their expected expression level or amount of cell. These results can determine whether there are enough and uniform coverage across the microscope slide surface, or whether the samples antigen were retrieved properly (especially on enzymatic antigen retrieval methods for large tissue samples).

In other embodiments, positive control samples which contain two or more different kinds of biomarkers, e.g., antigen, are included on the microscope slide. In these embodiments, each of the positive control samples may also contain different antigen levels. For example, different cell lines with different levels of protein expression may be chosen to generate individual cell pellets. Alternatively, cell lines containing different kinds of antigen may be chosen such that each different cell pellet contains different amount of cells. These cell pellets may be arranged in a pre-determined pattern about the sample-affixing area. These positive control samples may be quantified and the results compared to their expected expression level.

For multiplexed experiments, multiple cell pellets may be used to ensure a range of staining intensity over all markers. In such a case, the controls may be selected and arrayed on the slide in a pattern designed to allow the estimation of the spatial patterns for all markers.

In addition to positive control samples with different biomarker levels or different kinds of biomarkers, a negative control sample may be added as well. Thus, in certain embodiments, the microscope slide of the present invention may contain both positive and negative control samples. The microscope slide of the present invention may therefore comprise one or more negative control samples affixed on the first major surface at locations adjacent to sample-affixing area.

Table 1 presents exemplary cell lines useful for generating cell pellet controls according to certain embodiments of the invention. The cell lines have different levels of HER2 expression.

TABLE 1

Cell line and related Her2 protein expression.

| Cell line | Her2 protein pg/μg of lysate* | Usage |
| --- | --- | --- |
| BT-474 | 3826.3 | Strong positive control |
| SK-BR-3 | 2700 | |
| MDA-MB-361 | 852.3 | Medium positive control |
| MDA-MB-453 | 528.6 | |
| MDA-MB-231 | 157.6 | |
| MCF-7 | 110 | |
| K562 | — | Negative control |

*McCabe, A., et al., Automated Quantitative Analysis (AQUA) of In Situ Protein Expression, Antibody Concentration, and Prognosis. Journal of the National Cancer Institute, 2005. 97(24): p. 1808-1815.

Figure 11:
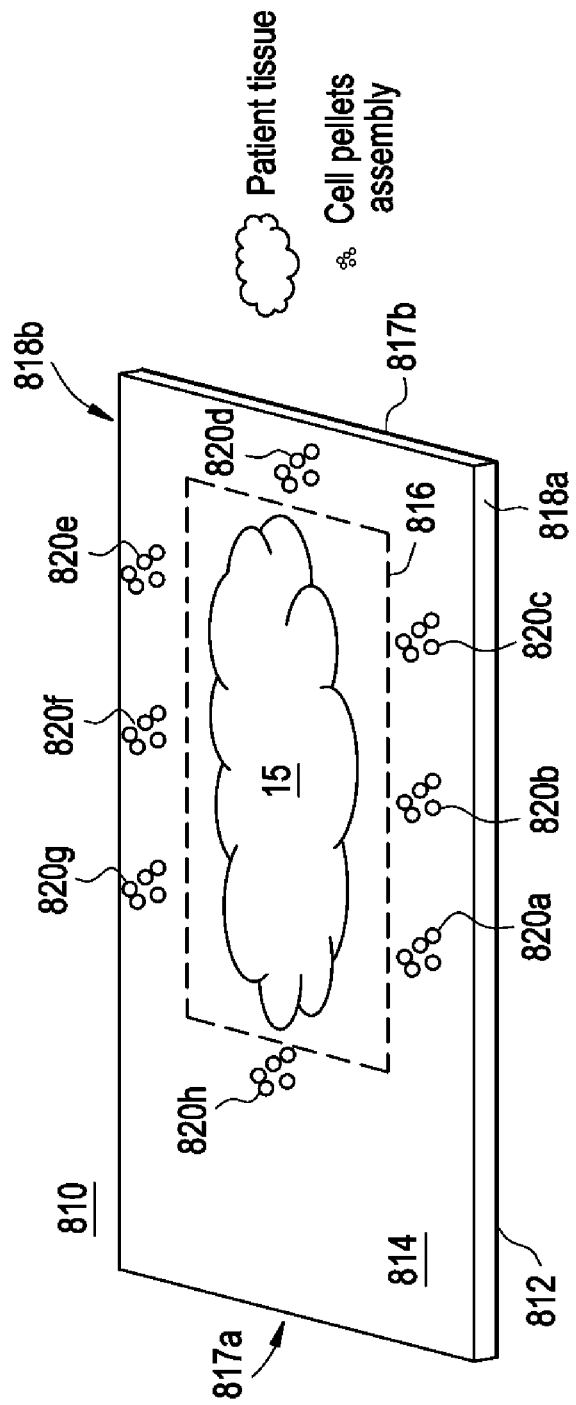
FIG. 11 depicts an alternative slide according to an embodiment of the present invention having a tissue-affixing area perimetrically-bounded by substantially evenly-spaced cell pellets.

FIG. 11 depicts still another microscope slide 810 of the present invention. Once again, like numbering denotes like components. Slide 810 includes a substantially planar substrate 812 including a first major surface 814 having a tissue sample-affixing area 816 for receiving a tissue sample 15 to be analyzed. Slide 810 further includes eight control samples 820a through 820h positioned at eight locations on surface 814, respectively. As shown in FIG. 11, the microscope slide 810 includes a tissue-affixing area perimetrically-bounded by substantially evenly-spaced cell pellets.

Figure 12:
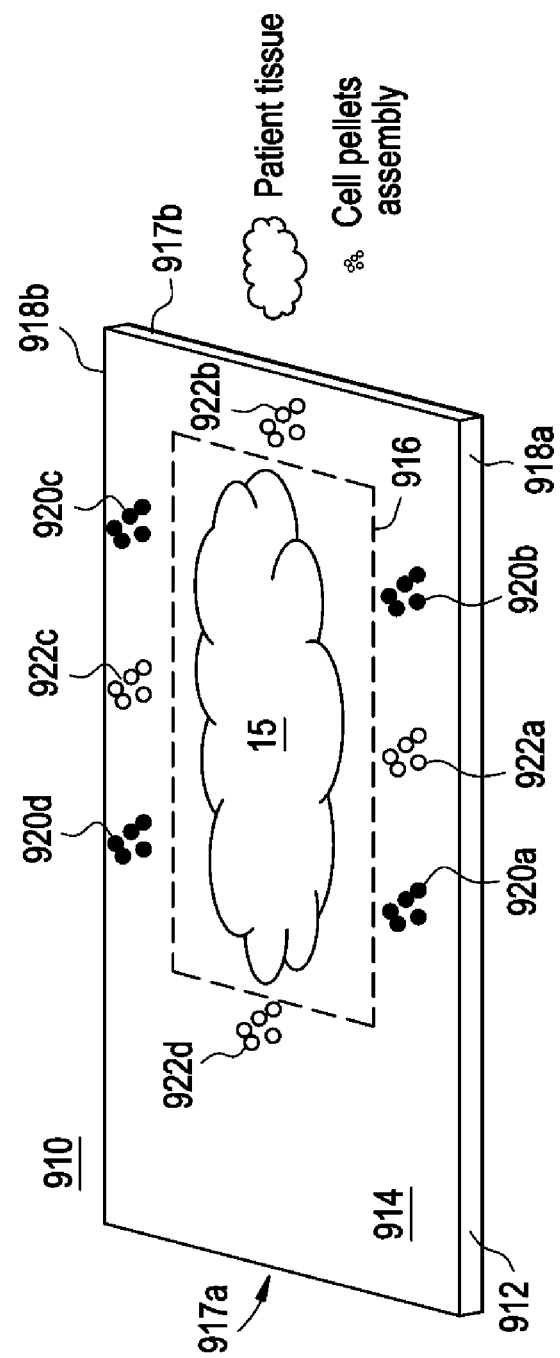
FIG. 12 depicts another alternative slide according to an embodiment of the present invention having a tissue-affixing area perimetrically-bounded by different types of pellets.

FIG. 12 depicts yet another microscope slide 910 of the present invention, with like numbering denoting like components. Slide 910 includes a substantially planar substrate 912 including a first major surface 914 having a tissue sample-affixing area 916 for receiving a tissue sample 15 to be analyzed. Slide 910 further includes eight control samples 920a through 920d and 922a through 922d, alternately positioned at eight locations on surface 914, respectively. As shown in FIG. 12, microscope slide 910 includes a tissue-affixing area perimetrically-bounded by substantially evenly-spaced cell pellets. Desirably, positive control samples 920a-d contain a common biomarker that may be detected by the same detection means. Similarly, control samples 922a-d may contain a common biomarker different from the common biomarker of 920ad. Alternatively, the control samples 922a-d may contain the same biomarker as that of the positive control samples, albeit at a different detection level. The control samples 922ad may also serve as negative controls as compared to that of positive control samples 920a-d.

Figure 13:
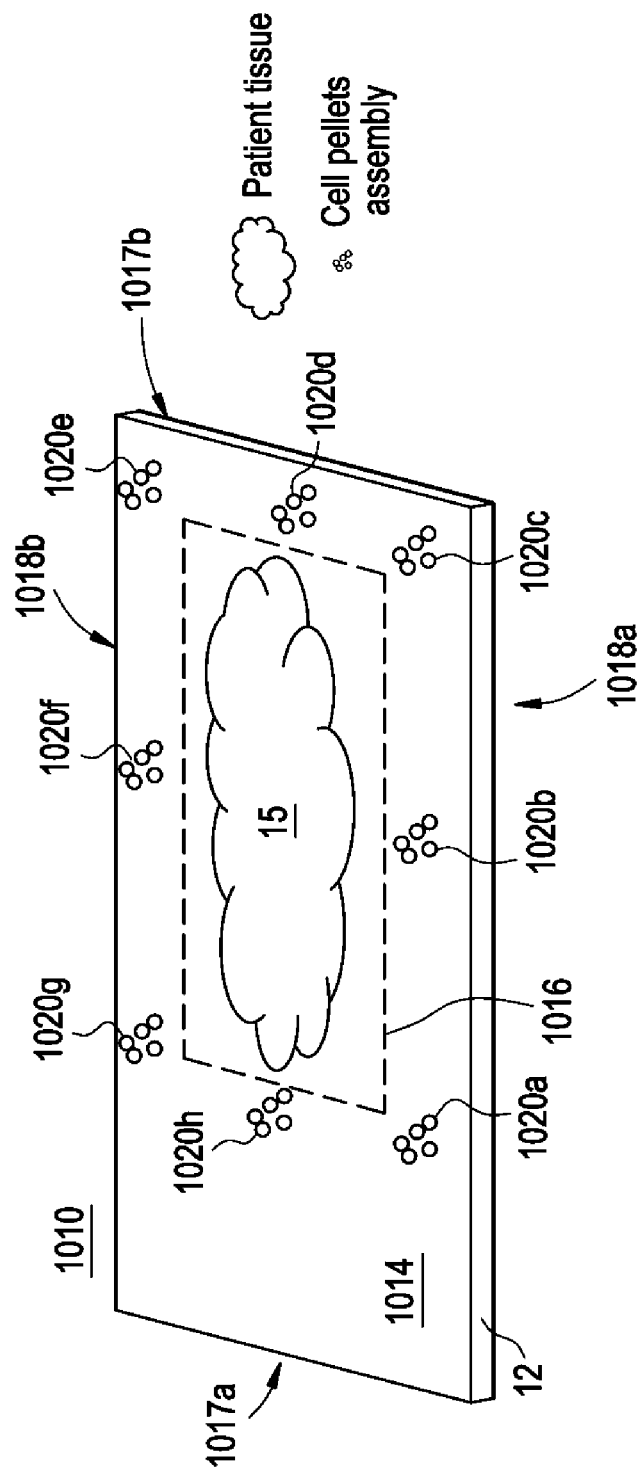
FIG. 13 depicts a slide according to an embodiment of the present invention having eight cell pellets about a tissue-affixing area on a slide.

FIG. 13 depicts yet another microscope slide 1010 of the present invention. Slide 1010 includes a substantially planar substrate 1012 including a first major surface 1014 having a tissue sample-affixing area 1016 for receiving a tissue sample 15 to be analyzed. Slide 1010 further includes eight positive control samples 1020a through 1020h, positioned at eight locations on surface 1014, respectively. As shown in FIG. 13, control samples 1020a, 1020h and 1020g are positioned between tissue sample 15 and the longitudinal edge 1017a, and form a line segment parallel the longitudinal edge 1017a. Control sample 1020h is also positioned substantially in the middle between control samples 1020a and 1020g. Similarly, control samples 1020c, 1020d and 1020e are positioned between tissue sample 15 and the longitudinal edge 1017b, and form a line segment parallel the longitudinal edge 1017b. Control sample 1020d is also positioned substantially in the middle between control samples 1020c and 1020e.

As shown in FIG. 13, control sample 1020b is positioned substantially in the middle between control samples 1020a and 1020c. Control samples 1020a, 1020b and 1020c are positioned between tissue sample 15 and edge 1018a, and substantially form a line segment parallel edge 1018a. Control sample 1020f is positioned substantially in the middle between control samples 1020e and 1020g. Control samples 1020e, 1020f and 1020g are positioned between tissue sample 15 and edge 1018b, and substantially form a line segment parallel edge 1018b.

Figure 14:
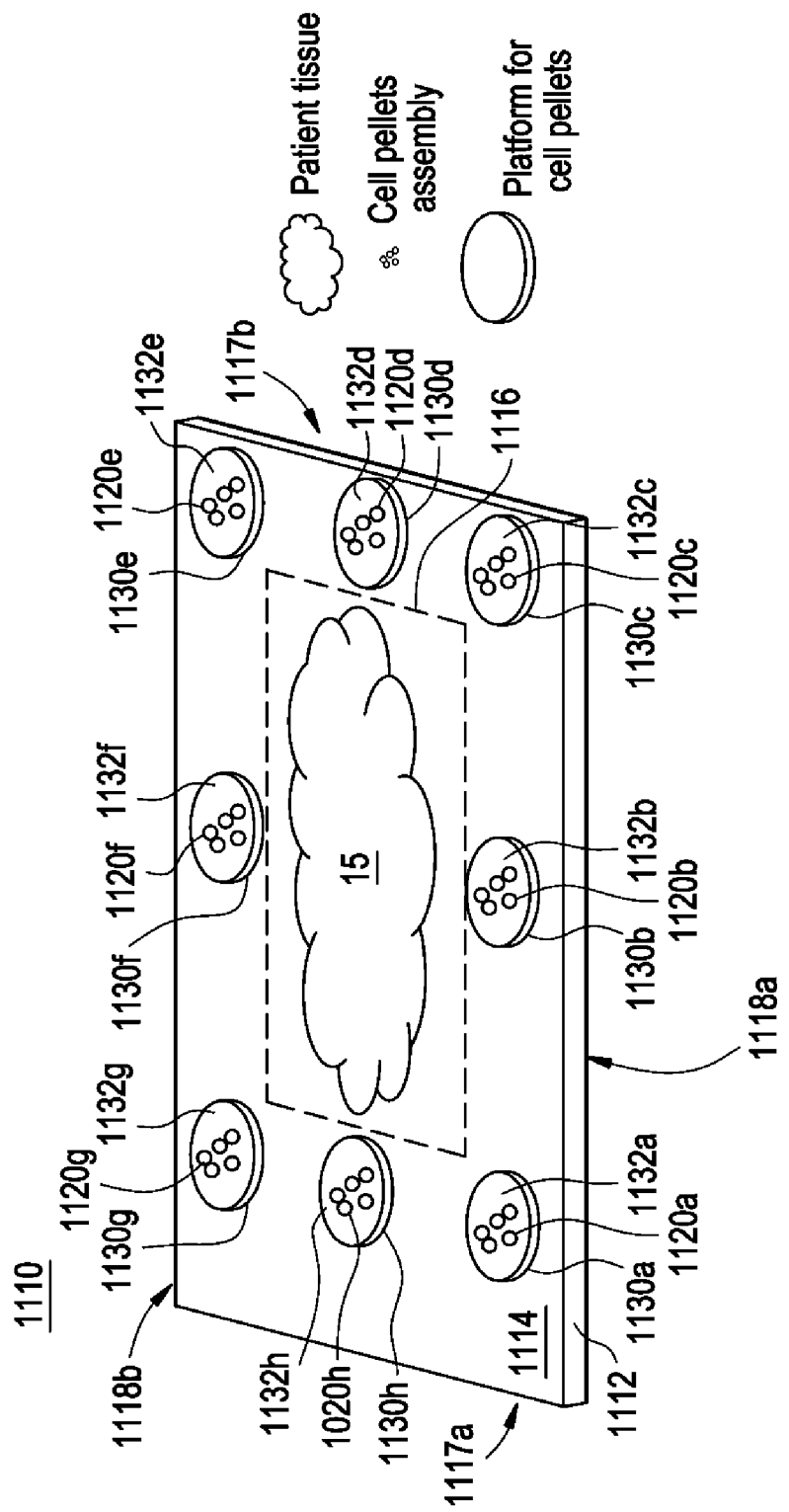
FIG. 14 depicts yet another alternative slide according to an embodiment of the present invention in which the cell pellets positioned about the tissue-affixing area of the slides are further provided on support platforms on the first major surface of the microscope slide.

FIG. 14 depicts yet another microscope slide 1110 of the present invention with like numbering denoting like components. Slide 1110 includes a substantially planar substrate 1112 including a first major surface 1114 having a tissue sample-affixing area 1116 for receiving a tissue sample 15 to be analyzed. Slide 1110 further includes eight positive control samples 1120a through 1120h positioned about sample-affixing area 1116. Further, slide 1110 includes substantially planar platforms 1130a-h affixed to major surface 1114, each providing a substantially planar platform surface 1132a-h, respectively. Each platform surface 1132a-h thus each supports a control sample 1120a-h thereon, respectively. Platform surfaces 1132a through 1132h are elevated above the first major surface 1114 such that if control samples 1120a-h each indicate successful staining, there will be a still greater confidence that tissue sample 15 was also properly stained, particularly when slide 1110 is oriented face-up (i.e., first major surface 1114 facing upwards) during staining. Desirably, platforms 1130a-h have a thickness greater than a tissue sample, however the present invention contemplates that any thickness will provide enhanced confidence of staining.

Control samples 1120a, 1120h and 1120g (as well as the platforms 1130a, 1130h and 1130g) are positioned between tissue sample 15 and the longitudinal edge 1117a, and form a line segment parallel the longitudinal edge 1117a. Control sample 1120h is also positioned substantially in the middle between control samples 1120a and 1120g. Similarly, control samples 1120c, 1120d and 1120e (as well as the platforms 1130c, 1130d and 1130e) are positioned between tissue sample 15 and the longitudinal edge 1117b, and substantially form a line segment parallel the longitudinal edge 1117b. Control sample 1120d is also positioned substantially in the middle between control samples 1120c and 1120e.

Control sample 1120b is positioned substantially in the middle between control samples 1120a and 1120c. Control samples 1120a, 1120b and 1120c are positioned between tissue sample 15 and edge 1118a, and form a line segment parallel edge 1118a. Control sample 1120f is positioned substantially in the middle between control samples 1120e and 1120g. Control samples 1120e, 1120f and 1120g are positioned between tissue sample 15 and edge 1118b, and substantially form a line segment parallel edge 1118b.

Figure 15:
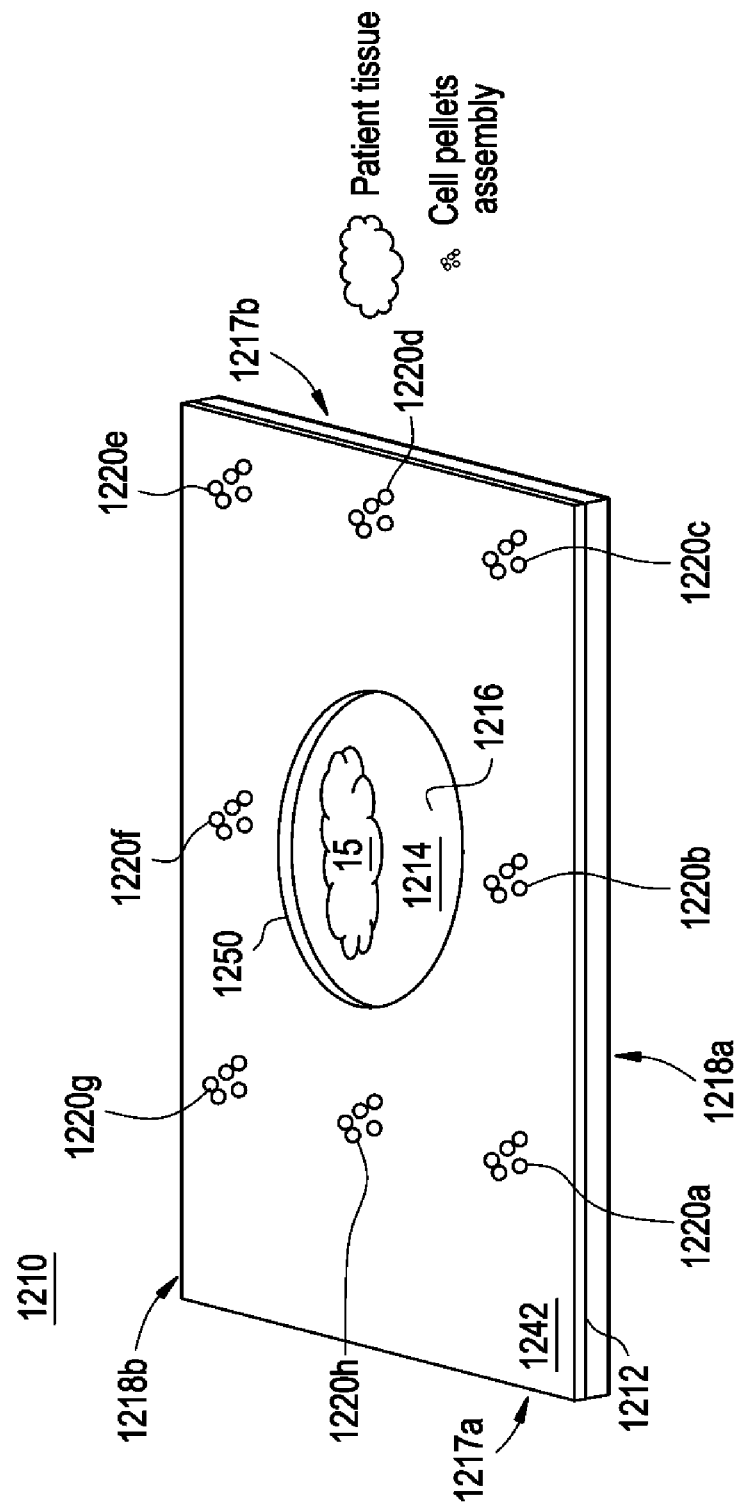
FIG. 15 depicts yet another alternative slide according to an embodiment of the present invention having cell pellets positioned about the tissue-affixing area of the slide, where the tissue sample is affixed within a planar recessed area on the first major surface of the microscope slide.

FIG. 15 depicts yet another microscope slide 1210 of the present invention with like numbering denoting like components. Slide 1210 includes a substantially planar substrate 1212 including an applied planar substrate platform 1240. Applied substrate platform includes a platform surface 1242 and an aperture 1250 in open registry with first major surface 1214 of substrate 1212. Major surface 1214 includes a tissue sample-affixing area 1216 exposed through aperture 1250 for receiving a tissue sample 15 to be analyzed. Slide 1212 further includes eight positive control samples 1220a-h, positioned on the platform surfaces 1242 about aperture 1250. Aperture 1250 and first major surface 1214 define a planar recessed area for affixing the tissue sample. As shown in FIG. 15, control samples 1220*a*, 1220*h* and 1220*g* are positioned between tissue sample 15 and longitudinal edge 1217*a*, and substantially form a line segment parallel the longitudinal edge 1217*a*. Control sample 1220*h* is also positioned substantially in the middle between control samples 1220*a* and 1220*g*. Similarly, control samples 1220*c*, 1220*d* and 1220*e* are positioned between tissue sample 15 and the longitudinal edge 1217*b*, and substantially form a line segment parallel the longitudinal edge 1217*b*. Control sample 1220*d* is also positioned substantially in the middle between control samples 1220*c* and 1220*e*.

Control sample 1220*b* is positioned substantially in the middle between control samples 1220*a* and 1220*c*. Control samples 1220*a*, 1220*b* and 1220*c* are positioned between tissue sample 15 and edge 1218*a*, and form a line segment parallel edge 1218*a*. Control sample 1220*f* is positioned substantially in the middle between control samples 1220*e* and 1220*g*. Control samples 1220*e*, 1220*f* and 1220*g* are positioned between tissue sample 15 and edge 1218*b*, and form a line segment parallel edge 1218*b*. The present invention further contemplates that substrate platform 1240 may further define an elongate channel (not shown) extending in fluid communication from aperture 1250 to an edge of substrate 1212 so as to assist drainage of the stain from sample-affixing area 1216 after staining. When slide 1210 is stained such that major surface 1214 is in a face-up orientation, the relative height between sample-affixing area 1216 and platform surface 1242 provides further confidence of proper staining of tissue sample 15 when all of control samples 1220*a-h* indicate they have been stained.

Figure 16:
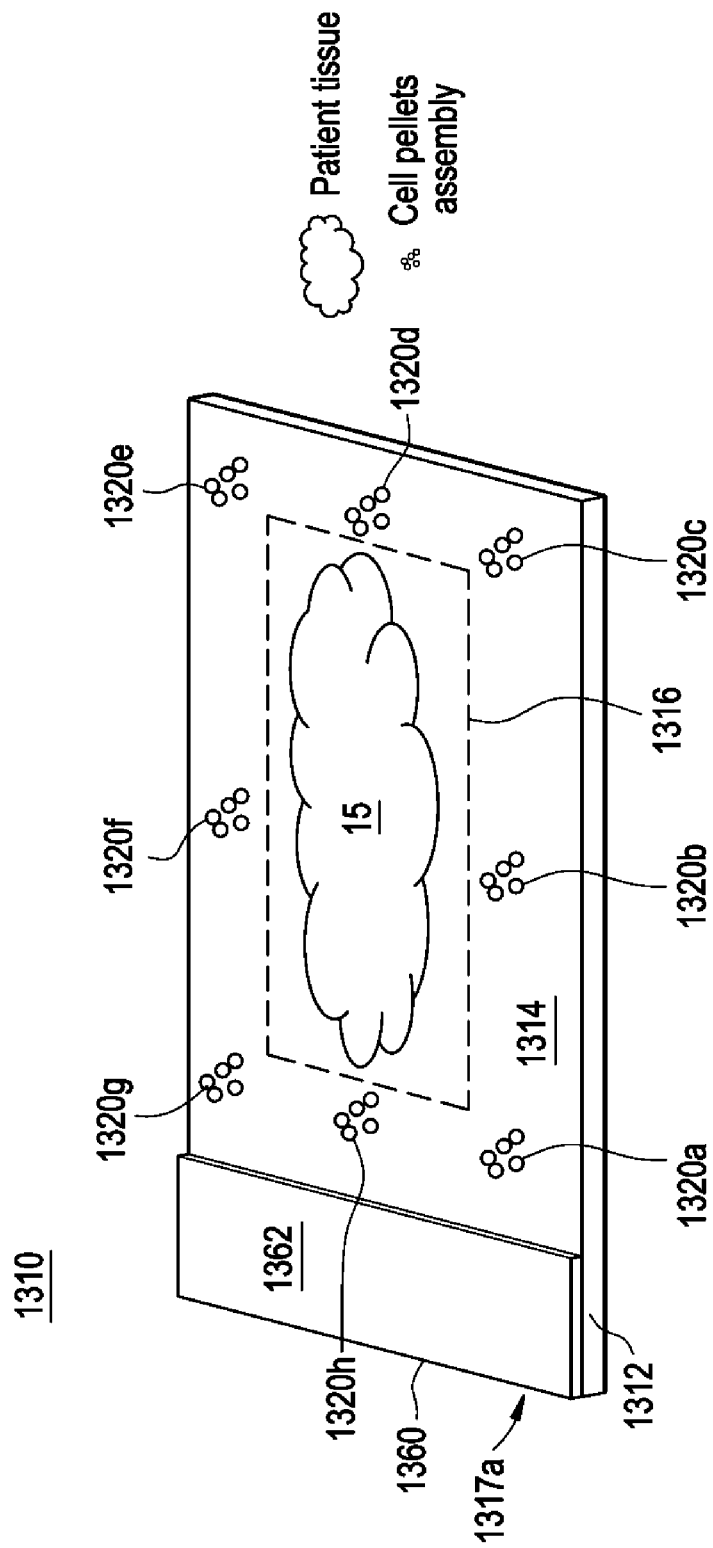
FIG. 16 depicts yet another alternative slide according to an embodiment of the present invention having cell pellets positioned about the tissue-affixing area of the slide, the microscope slide further comprises a substantially planar label area elevated above sample-affixing area.

FIG. 16 depicts yet another microscope slide 1310 of the present invention with like numbering denoting like components. Slide 1310 includes a substantially planar substrate 1312 including a first major surface 1314 having a tissue sample-affixing area 1316 for receiving a tissue sample 15 to be analyzed. Slide 1310 further includes eight positive control samples 1320*a-h*, positioned at eight locations on surface 1314, respectively, generally as described for slide 1010 in FIG. 13. Slide 1310 further comprises a label 1360 affixed to major surface 1314. Label 1360 includes a label surface 1362 on which indicia such as information pertaining to the slide, the tissue sample, or the staining process are printed. Such indicia may further be provided by a bar code either printed on surface 1362 or by another label affixed thereto. As shown in FIG. 16, the label 1360 is situation between the longitudinal edge 1317*a* and the control samples 1320*a*, 1320*h* and 1320*g*. The present invention contemplates that a label similar to label 1360 may be similarly provided on any slide embodying the present invention.

In another aspect, the invention provides a kit for tissue sample analysis. The kit includes one or more microscope slides according to certain embodiments of the invention. The slides are adapted to receive a tissue sample to be analyzed. Desirably, the slides are also adapted to receive a label including indicia related to the analysis to be performed. The kit may also include a user manual to provide information about the slides and to instruct on the proper use of the slides.

In another aspect, the invention provides a method of fabricating a microscope slide according to aspects of the invention, which method comprises transferring and affixing a thin layer of a positive control sample onto the microscope slide at at least a first location and a second location. Preferably, the slides used are charged slides. Preferably, after the transferring and affixing of the thin layer of a positive control sample onto the microscope slide, a subsequent baking step is included.

In certain embodiments, the thin layer control sample is an about 5 microns section of a sample.

In certain embodiments, the positive control sample comprises cell pellets. Preferably, the cell pellets comprise formalin-fixed cells suspended in melted paraffin wax.

Figure 17:
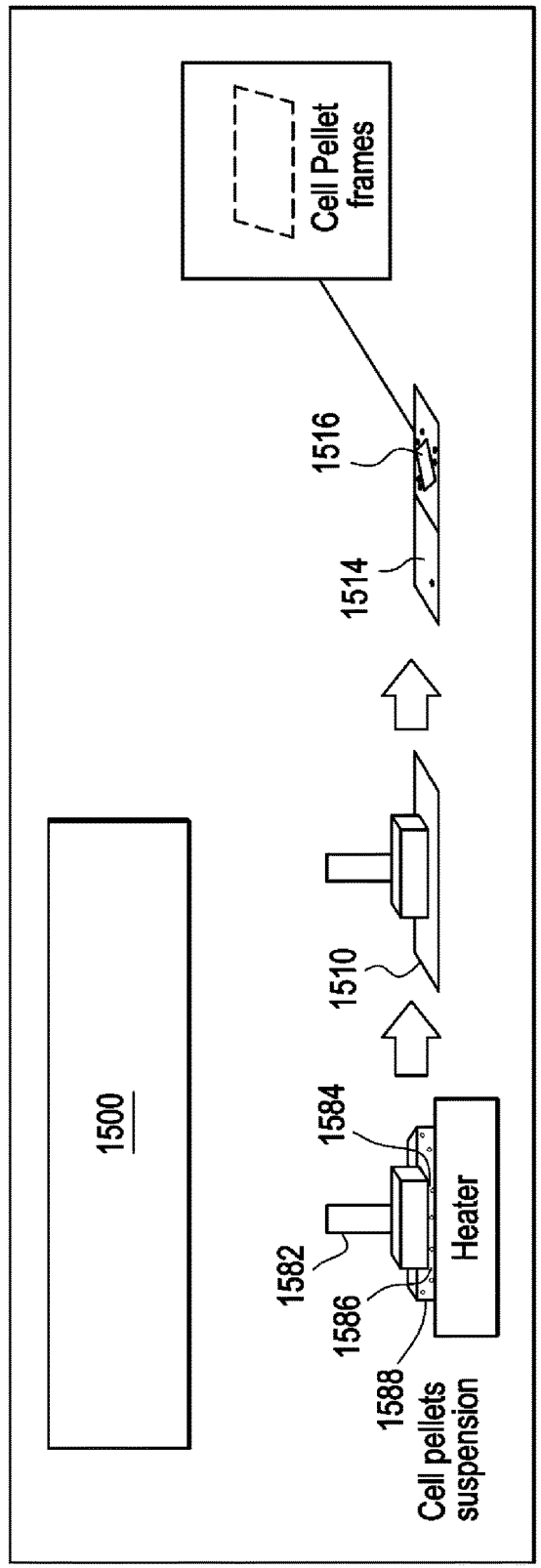
FIG. 17 depicts a system for fabricating a slide according to an embodiment of the present invention.

FIG. 17 depicts a system 1500 for affixing control samples to a microscope slide of the present invention. System 1500 includes a stamp 1582 having a substantially planar print head face 1584 having one or more print heads 1586 protruding therefrom. Print heads 1586 provide a planar surface for holding an amount of control sample material to be deposited on the major surface of a slide. System 1500 dips print heads 1586 in a reservoir 1588 containing melted paraffin wax and a suspension of formalin-fixed cell pellets. The cell pellets will adhere to the print heads 1586. System 1500 then transfers stamp 1582 to major surface 1514 of a slide 1510. Stamp 1582 is brought into contact with surface 1514 so as to effect transfer of the cell pellets to major surface 1514. Print heads 1586 are arrayed on print face 1584 so as to deposit the cell pellets at the locations corresponding to the control samples of the present invention about the sample-affixing area 1516 of slide 1510. As is known in the art, the slides may be charged to better enable transfer of the cell pellets. Additionally, the present invention contemplates that the slides would then be baked to affix the control samples in place. The present invention further contemplates that different print heads may be employed, having differently arrayed print heads so as to deposit control samples comprising different markers in other available locations about the sample-affixing area of the slide. Typically, the thickness of the deposited cells is on the order of about 5 microns for monolayer of cells, which is roughly equivalent to the thickness of a tissue section affixed to the slide. This contact printing method is high throughput, simple and low cost.

Other methods for depositing the control samples onto the slides of the present invention include, for purposes of illustration and not of limitation, use microdispense technique to add aliquots of formalin-fixed cell pellet in melted wax solution onto the slide. Alternatively, the cells of the control samples may be formalin-fixed and paraffin embedded in slide-sized block. The entire slice from the block may be placed onto the slide and the sample-affixing area later carved out by mechanical or chemical means. Alternatively still, the block may be cored-out so as to define an aperture in the shape of the sample-affixing area of the slide so that only the perimetrical outline of the sample-affixing area is applied to the slide.

In another aspect, the invention provides a method of analysis.

In one embodiment, the method of analysis comprises staining a microscope slide according to an embodiment of the invention with a detection means for the positive control sample; and detecting the positive control sample from the at least first and second location.

In certain embodiments, the presence of signals from all the locations of the positive control samples provides real-time confirmation of staining quality. Accordingly, the absence of signals from some locations of the positive control samples indicates staining failure.

In certain embodiments, the slide further comprising one or more negative control sample affixed on the first major surface at locations adjacent to sample-affixing area 16, and wherein the presence of signals from some locations of the negative control samples indicates staining failure.

In certain embodiments, the microscope slide further comprises a tissue sample.

In certain embodiments, the positive control samples are cell pellets and the detecting step comprises masking out portions of the image not containing cell pellets, and accounting for the localization of the marker inside each cell of the cell pellets. Preferably, the method further comprises a step of performing a two-compartment image segmentation which delineates the nucleus of each cell plus an annular region around each nucleus of each cell of the cell pellet. Preferably, the method further comprises a step of measuring the average staining of each marker in both compartments of each cell of the cell pellets in the field-of-view, and summarizing these cell-level metrics to produce an overall field-of-view metric. The field-of-view metric may comprise average nuclear expression of a known nuclear marker. More preferably, the method further comprises detecting artifacts by examining the coefficients in a linear statistical model, and estimating spatial staining artifacts using the linear statistical model where the response is the field-of-view level staining metric for each cell pellet and the predictors are the two spatial dimensions of the slide. Even more preferably, the method further comprises a step of correcting minor spatial artifacts by using the fitted model to estimate and subtract out uneven staining profiles.

While the particular embodiment of the present invention has been shown and described, it will be apparent to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A microscope slide for a tissue sample, said slide comprising:
   an elongate planar substrate comprising a first major surface having a sample-affixing area arranged to receive an affixable tissue sample, wherein the sample-affixing area does not have the affixable tissue sample disposed thereon;
   a first positive control sample affixed on said first major surface at a first location adjacent to said sample-affixing area; and
   a second positive control sample affixed on said first major surface at a second location adjacent to said sample-affixing area;
   wherein the first and second locations are spaced such that a staining quality of said first and second positive control samples is indicative of a staining quality of the tissue sample, wherein said first and second locations are on opposing sides of said sample-affixing area and wherein a perimeter of said sample-affixing area is defined by a line on the major surface or a microchannel etched into the major surface.

2. The microscope of claim 1, wherein the first and second locations are spaced such that at least a portion of said sample-affixing area extends between said first and second locations along the longitudinal axis of said substrate.

3. The microscope slide of claim 1, wherein at least one of said first and second locations are located transversely alongside said sample-affixing area.

4. The microscope slide of claim 1, wherein at least one of said first and second locations are transversely-located between said sample-affixing area and an elongate edge of said substrate.

5. The microscopic slide of claim 1, wherein said first and second locations are diametrically across from said sample affixing area.

6. The microscope slide of claim 1, further comprising a third positive control sample affixed on said first major surface at a third location adjacent to said sample-affixing area.

7. The microscope slide of claim 6, further comprising a fourth positive control sample affixed on said first major surface at a fourth location adjacent to said sample-affixing area.

8. The microscope slide of claim 7, further comprising one or more positive control samples affixed on said first major surface at one or more other location adjacent to said sample-affixing area.

9. The microscope slide of claim 1, wherein three or more positive control samples are substantially-equally spaced along the perimeter of said sample-affixing area.

10. The microscope slide of claim 1, wherein the two or more positive control samples form a continuous line that surrounds the entire perimeter of said sample-affixing area.

11. The microscope slide of claim 1, wherein the positive control samples are selected from a groups consisting of cell pellet, control tissue sample, or carrier loaded with biomaterials.

12. The microscope slide of claim 1, wherein the positive control samples and the tissue sample include the same biomarker.

13. The microscope slide of claim 12, wherein the detection means is an immunoassay and wherein the positive control sample and the tissue sample comprise the same kind of antigen biomarker.

14. The microscope slide of claim 1, wherein the first and second positive control samples contain a biomarker in common.

15. The microscope slide of claim 1, wherein the first and second positive control samples contain different biomarkers, and the controls are both detectable when the tissue sample is analyzed.

16. The microscope slide of claim 1, further comprising one or more negative control samples affixed on said first major surface at locations adjacent to said sample-affixing area.

17. The microscope slide of claim 1, wherein each control sample comprises a biomarker which include a corresponding paired associate biomarker in another control positioned across a portion of the tissue-affixing area of the slide substrate.

18. The microscope slide of claim 17, wherein the two paired associate biomarkers are the same biomarker.

19. The microscope slide of claim 17, wherein the two paired associate markers are different, and are both capable of been detected when the tissue sample is analyzed.

20. The microscope slide of claim 1, wherein each control sample contains two or more different kinds of biomarkers.

21. The microscope slide of claim 1, wherein said slide comprises three or more control samples about the tissue affixing area, and at least two of the control samples which are located across a portion of the tissue-affixing area include a common biomarker.

22. The microscope slide of claim 1, wherein control samples comprising different amounts of a biomarker are included on the microscope slide, and are provided in at least pairs such that the pairs of like control samples are located across some portion of the tissue-affixing area.

23. The microscope slide of claim 1, wherein at least one of said control samples is elevated above said sample-affixing area.

24. The microscope slide of claim 23, further comprising at least one support platform positioned on said first major surface at said locations where the control samples are located, said support platform comprising a support surface elevated above said first major surface, wherein said at least one control samples is affixed to said support surface.

25. The microscope slide of claim 23, wherein said sample-affixing area further comprises a planar recessed area, said substrate defining a recess extending in fluid communication from said planar recessed area and opening on said first major surface.

26. The microscope slide of claim 1, wherein said substrate further comprises a substantially planar label area elevated above said sample-affixing area.

27. A kit, comprising a microscope slide according to claim 1 adapted to receive a tissue sample to be analyzed.

28. The kit according to claim 27, wherein the slides are further adapted to receive a label including indicia related to the analysis to be performed.

* * * * *